(12) United States Patent
Bush et al.

(10) Patent No.: US 7,878,988 B2
(45) Date of Patent: Feb. 1, 2011

(54) METHOD FOR MEASURING THE STRENGTH OF HEALING BONE AND RELATED TISSUES

(76) Inventors: Stephen Thomas Bush, 220 Keafer Rd., Johnstown, PA (US) 15905; Stephen Francis Bush, 9 Sable Ter., Latham, NY (US) 12110

( * ) Notice: Subject to any disclaimer, the term of this patent is extended or adjusted under 35 U.S.C. 154(b) by 1117 days.

(21) Appl. No.: 11/544,248

(22) Filed: Oct. 6, 2006

(65) Prior Publication Data
US 2008/0161729 A1    Jul. 3, 2008

(51) Int. Cl.
*A61B 5/103*    (2006.01)
*A61B 17/80*    (2006.01)

(52) U.S. Cl. .......................... 600/587; 606/70; 606/76; 606/281

(58) Field of Classification Search .................. 73/779; 600/422, 587–588, 592, 594–595; 602/2; 606/54–59, 70–71, 76, 102, 129, 280–299, 606/902–913; 907/65–66; 977/734, 742, 977/842
See application file for complete search history.

(56) References Cited

U.S. PATENT DOCUMENTS

| | | | |
|---|---|---|---|
| 2,231,702 A * | 2/1941 | Burgwin et al. ............... | 73/779 |
| 4,576,158 A * | 3/1986 | Boland ........................ | 606/102 |
| 4,646,754 A * | 3/1987 | Seale ........................... | 600/587 |
| 4,920,806 A * | 5/1990 | Obama et al. ................ | 73/779 |
| 5,456,724 A | 10/1995 | Yen | |
| 5,695,496 A | 12/1997 | Orsak | |
| 6,034,296 A | 3/2000 | Elvin | |
| 6,755,831 B2 * | 6/2004 | Putnam et al. .............. | 606/311 |
| 6,809,462 B2 * | 10/2004 | Pelrine et al. ............... | 310/319 |
| 6,848,320 B2 * | 2/2005 | Miyajima et al. ............. | 73/763 |
| 6,872,403 B2 | 3/2005 | Pienkowski | |
| 2002/0049394 A1 * | 4/2002 | Roy et al. .................... | 600/594 |
| 2002/0166382 A1 * | 11/2002 | Bachas et al. ................. | 73/579 |
| 2005/0107870 A1 * | 5/2005 | Wang et al. ................ | 623/1.44 |
| 2006/0052782 A1 | 3/2006 | Morgan | |

OTHER PUBLICATIONS

McKinley, DW, Follow-up radiographs to detect callus formation after fractures, *Archives of Family Medicine*, vol. 9, pp. 373-374, 2000.

Chao, YS, et al., Biophysical stimulation of bone fracture repair, regeneration and remodeling, *European Cells and Materials*, vol. 6, pp. 72-85, 2003.

Blokhius, TJ, et al., Evaluation of strength of healing fractures with dual energy x-ray absorptiometry, *Clinical Orthopaedics and Related Research*, vol. 380, pp. 260-268, 2000.

(Continued)

*Primary Examiner*—Thomas C Barrett
*Assistant Examiner*—Larry E Waggle, Jr.

(57) ABSTRACT

A method of measuring healing strength of bone includes a bone fixation plate (14) implanted at the healing area between bone segments (12). The bone fixation plate (14) includes high aspect ratio material with electric current conduction properties responsive to strain. This method causes an induced, or directly applied, electric current to pass through the high aspect ratio material. Analysis of the change in this current by a series of increasing loads placed on the healing body part indicates what level of load produces strain on the bone fixation plate (14). As healing strength increases, evidence of strain on the bone fixation plate (14) occurs at a greater load. Physicians determine thereby the strength of bone healing and safe levels of activity for patients while bone healing progresses.

9 Claims, 4 Drawing Sheets

OTHER PUBLICATIONS

Siu, WS, et al., pQCT bone strength index may serve as a better predictor than bone mineral density for long bone breaking strength, *Journal of Bone and Mineral Metabolism*, vol. 21, pp. 316-322, 2003.

Ashe, MC, Accuracy of pQCT for evaluating the aged human radius: an ashing, histomorphometry and failure load investigation, *Osteoporosis International*, vol. 17, pp. 1241-1251, 2006.

Singh, VR, et al., Early detection of fracture healing of a long bone for better mass health care, *Proceedings of the 20th Annual International Conference of the IEEE Engineering in Medicine and Biology Society*, vol. 20, pp. 3.17-3.18, 1998.

Asai, H, et al., Noninvasive evaluation of bone stiffness by combining microdefocusing method and reflectance method, *Proceedings of the 1998 IEEE Ultrasonic Symposium*, vol. 2, pp. 1459-1462, 1998.

Behari, J, Mechanism of accelerated bone fracture healing, *Proceedings of the 20th Annual International Conference of the IEEE Engineering in Medicine and Biology Society*, vol. 6, pp. 2928-2930, 1998.

Yang, GY, et al., Fabrication and characterization of microscale sensors for bone surface strain measurement, *Proceedings of IEEE Sensors*, vol. 3, pp. 1355-1358, 2004.

Fritton, SP, The in vivo mechanical loading history of bone, *Proceedings of the First Joint Conference of the Engineering in Medicine and Biology Society and the Biomedical Engineering Society*, vol. 1, p. 501, 1999.

Turner, CH, Mechanical loading effects on bone cells, *Proceedings of the First Joint Conference of the Engineering in Medicine and Biology Society and the Biomedical Engineering Society*, vol. 2, p. 1300, 1999.

Balasundaram, G, et al., Nanomaterials for osteoporosis treatment, *Proceedings of the IEEE 31st Annual Northeast Bioengineering Conference*, pp. 170-171, 2005.

* cited by examiner

METHOD FOR MEASURING THE STRENGTH OF HEALING BONE AND RELATED TISSUES

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

FIELD OF INVENTION

This invention relates to biomedical implants and, more importantly, to a system for monitoring the strength of a healing, bone, joint, or ligament union while an orthopedic fixation device such as a plate, pin, or screw is in place.

BACKGROUND OF THE INVENTION

Bone fractures heal in progressive, complex, sequential steps at the cellular level. The healing process produces osteoid, the precursor of new bone, which eventually undergoes calcification and new bone formation. As healing progresses, the strength of the healing area increases. This same process occurs when physicians operatively stabilize a bone fracture by implanting a bone fixation device such as a plate, pin, or screw. Physicians use similar bone fixation devices after resecting diseased bone and tissue. Another option is to substitute a portion of cadaver bone for the resected bone using an implanted bone fixation device to stabilize the bone junction until healing occurs.

Bone healing takes months for completion, depending on many variables, some of which are unknown and uncontrollable. During the healing process, the repaired area is subject to injury by excessive load applied to the area; yet, studies show that some load to the area promotes healing. Currently, physicians most often monitor bone healing by observing the increase in tissue density and calcification in a series of x-rays. X-rays are subjectively interpreted, frequently inconclusive, and tell little about the strength of the healing repair. Similar limitations apply to special imaging studies such as dual energy x-ray absorptiometry and peripheral quantitative computed tomography. Therefore, physicians must depend on clinical judgment and personal experience when advising patients on safe levels of activity, including movement and weight bearing, involving the repaired site.

Physicians need an objective measure of the degree of healing and strength of the union stabilized by the bone fixation device. Only then may physicians confidently advise patients on what level of effort by the patient the repair can safely bear. Equally important, physicians will avoid needlessly restricting patient activity because the safe level of activity is unknown, hoping to avoid injury to the repaired area. Detailed information on strength of healing not now available would significantly improve patient care and quality of life. Improvements in the cost of medical care would be significant but are beyond the scope of this patent application.

Several methods to measure bone strain received U.S. patents. The device of Yen, et al. described in U.S. Pat. No. 5,456,724 (1995) appears useful during surgery to install bone grafts but is not implantable for strain measurements during healing. The device of Orsak, et al. described in U.S. Pat. No. 5,695,496 (1997) measures light transmission through an optical fiber attached to an external bone fixation apparatus. This method is not applicable to commonly used implanted bone fixation procedures.

The system of Elvin, et al. described in U.S. Pat. No. 6,034,296 (2000) utilizes an implantable bone strain sensing system mounted on or in the bone fixation hardware. Some components must be hermetically sealed and mounted by adhesives to the bone fixation device. Eliminating the need for adhesives and seals and making the sensor system an integral part of the bone fixation device would improve reliability of operation. Vigorous manipulation sometimes necessary during surgical installation of the bone fixation device subjects all parts mounted on the bone fixation hardware to risk of damage during surgery. Also the added mass of foreign material introduced in the body comprising the mounted sensing system adds to the risk of complications during surgery and later recovery. Variations in the physical properties, such as density, of the attached materials comprising the sensing system compared to the properties of the bone fixation device increase the risk of implant failure. An ideal sensing system would be an integral part of the bone fixation device with no measurable increase in mass of foreign materials introduced into the body or variation in physical properties from the fixation device.

Morgan, et al. in U.S. Pat. App. No. 20060052782 described a monitoring system employing one or more sensors and microchips attached to a bone-fixation device. These attachments are subject to failure of adhesion to the fixation device, failure of seals protecting the components, and the danger of damage during surgical installation of the fixation device. Pressure and strain measurements from the discreet focus of the sensing site may not apply to the implant as a unit. Focal changes such as swelling or shrinkage of tissue during normal healing may confound readings intended to reflect forces on the entire fixation device. Sensor readings depend on radio frequency transmission, which is subject to interference and distortion in many environments. The ideal monitoring system would provide direct readings of strain on the fixation device as a single, bone-stabilizing unit with a sensing system integral to the fixation device.

The physical properties and electrical conduction characteristics of carbon nanotubes make them well suited to provide the basis for measuring the strength of healing of bone repairs. Since carbon nanotubes are molecular structures, they do not add any significant foreign mass to a bone fixation device. Carbon nanotubes may even add strength to a bone fixation device.

The diameter of a nanotube is on the order of a few nanometers (approximately 50,000 times smaller than the width of a human hair), while they can be up to several millimeters in length thus exhibiting a very high aspect ratio, referring to the ratio of length to width. The tubes occur naturally in random orientations and can be imbedded in or on various materials. Changes in tube length and/or orientation by even a micron or less alter the effective electrical resistance of the nanotube network. This alteration in electrical resistance is measured by current flow and indicates the stress and strain on the implant. Stress is the application of force per unit area on the implant; strain is the ratio of extension in length when loaded, to the original length of the implant.

BACKGROUND OF THE INVENTION

Objects and Advantages

Accordingly, the objects and advantages of the present invention are:
(a) to provide a method of obtaining objective data to indicate the magnitude of load a surgically repaired part can bear;
(b) to provide a healing indicator system that generates real-time data while a load is applied to the site of repair;
(c) to provide a healing indicator system that will allow physician and patient to determine maximum, safe load for the site of repair;
(d) to provide a healing indicator system without any significant additional foreign material inserted into the patient;
(e) to provide a healing indicator system that is an integral component of the bone fixation device without requiring special adhesives or seals; and
(f) to provide a healing indicator system that is not subject to damage during surgical installation.

Further objects and advantages will be apparent after considering the ensuing description and drawings.

SUMMARY

The present invention comprises a method to measure the strength of healing bone, joint, or ligament repairs when an orthopedic fixation device is used to stabilize the defective area.

DRAWINGS—FIGURES

Figure 1:
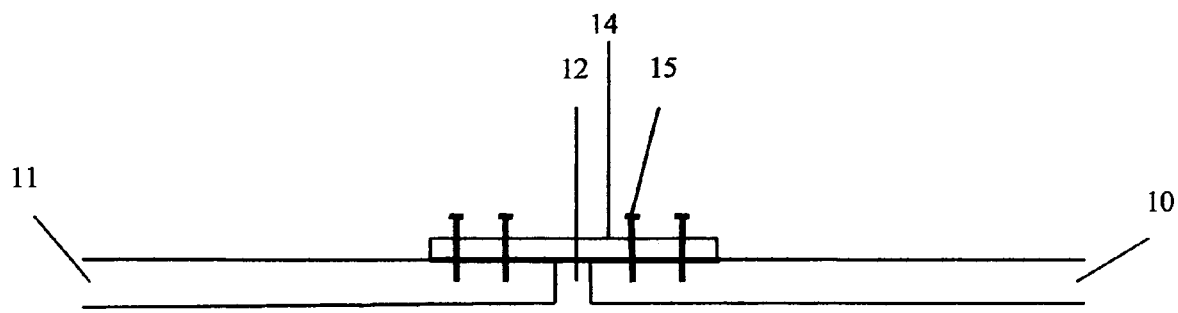
FIG. 1 depicts a bone repair stabilized by an implanted bone fixation plate.

| DRAWINGS -- REFERENCE NUMERALS | |
|---|---|
| 10 | Proximal healthy bone segment |
| 11 | Distal bone segment |
| 12 | Healing area between bone segments |
| 13 | Skin surface |
| 14 | Bone fixation plate |
| 15 | Attachment screw |
| 16 | Testing cuff |
| 16a | Active coil |
| 16b | Passive coil |
| 16c | Power source connector |
| 16d | Analyzer connector |
| 17 | Electric current source |
| 18 | Analyzer |

DETAILED DESCRIPTION OF THE PREFERRED EMBODIMENT

FIG. 1 illustrates, in longitudinal cross-section, implanted bone fixation plate 14 bridging a defect between proximal healthy bone segment 10 and distal bone segment 11. The unique property of bone fixation plate 14 is a component of carbon nanotubes.

Figure 2:
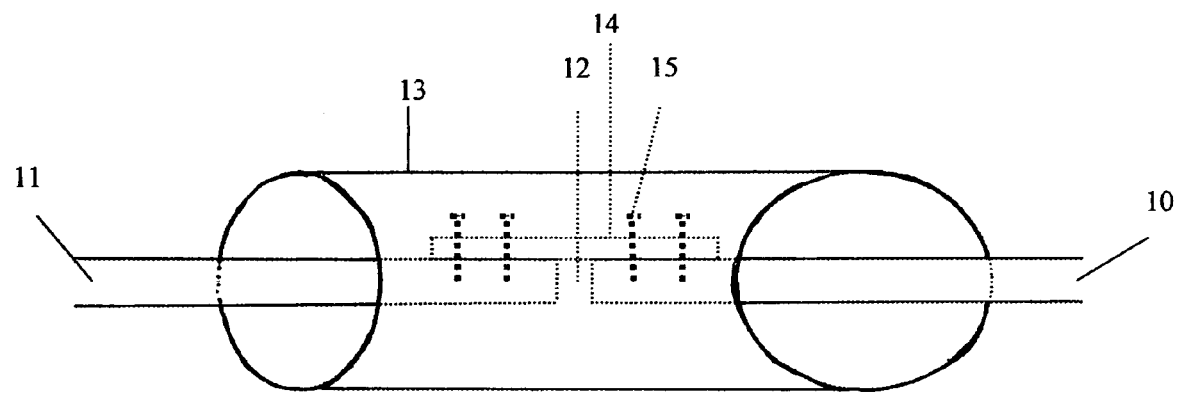
FIG. 2 depicts an extremity with a bone repair stabilized by an implanted bone fixation plate.

FIG. 2 depicts the bone repair of FIG. 1 located within the body, as in an extremity covered by skin surface 13.

Figure 3:
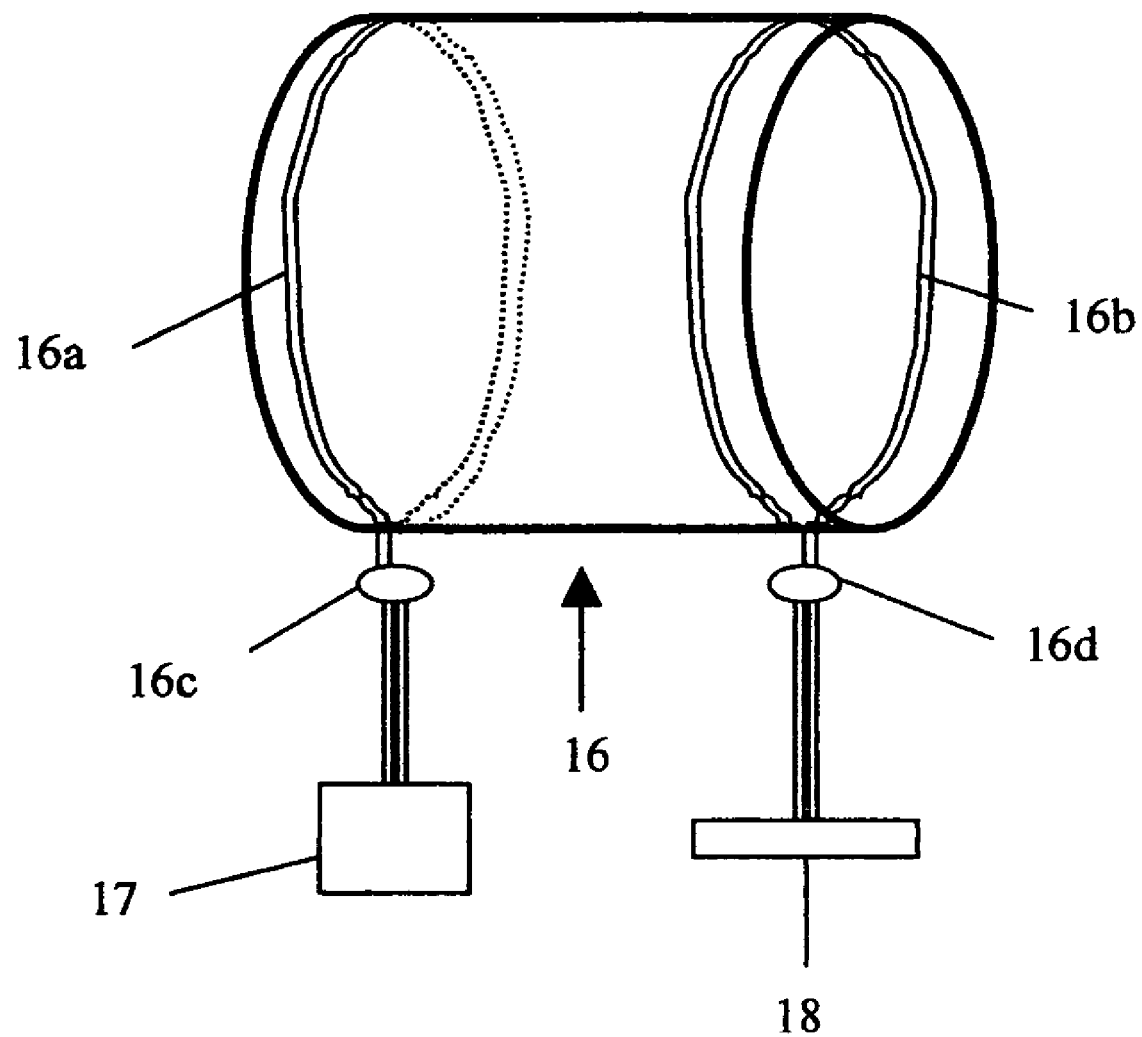
FIG. 3 depicts the testing cuff and connections.

FIG. 3 illustrates testing cuff 16 comprising two sets of electric coils. Active coil 16a and passive coil 16b both encircle the area of bone fixation plate 14 similar to a blood pressure cuff. Power source 17 attaches to active coil 16a via power source connector 16c. Analyzer 18 attaches to passive coil 16b via analyzer connector 16d.

Figure 4:
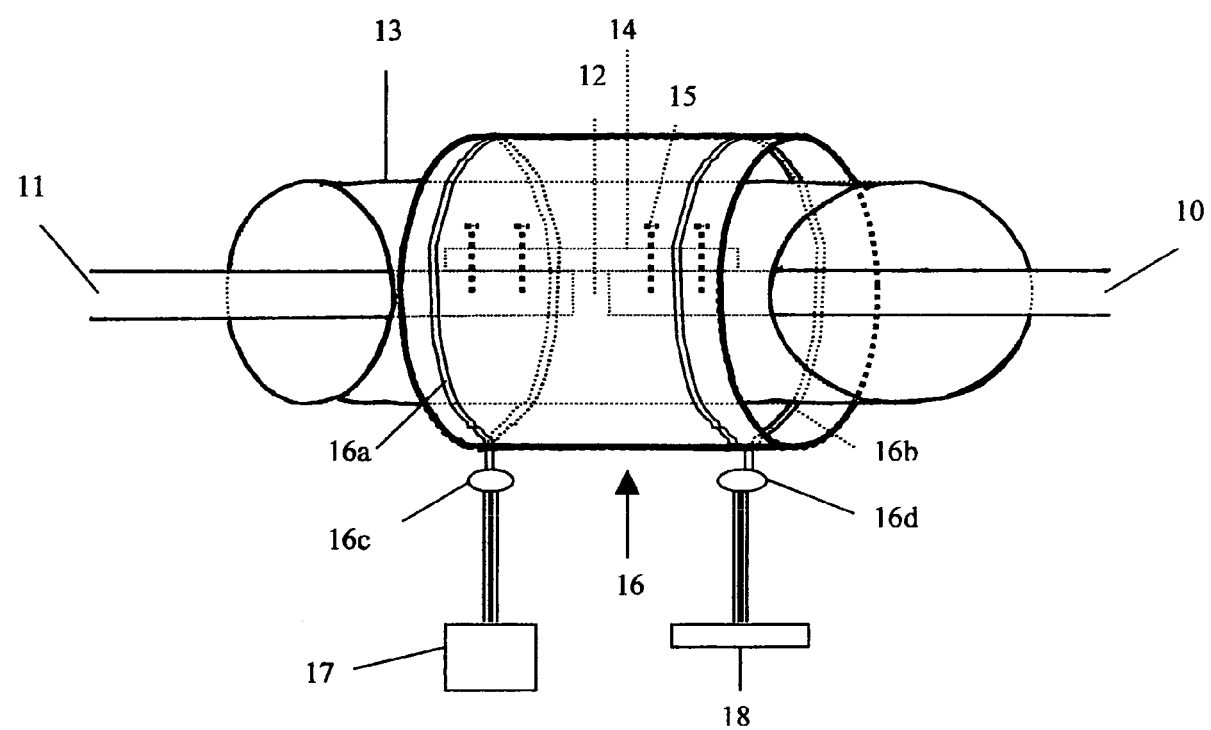
FIG. 4 depicts the testing cuff externally encircling an extremity with a bone repair stabilized by an implanted bone fixation plate.

FIG. 4 illustrates testing cuff 16 surrounding an extremity with a repaired bone as used for measuring the strength of healing area between bone segments 12.

Operation

Bone fixation plate 14 is implanted using a plurality of anchors such as attachment screw 15, as usually performed by surgeons skilled in the art. The bone healing process begins promptly, as described above. When the physician wishes to monitor the strength of healing area between bone segments 12, testing cuff 16 is placed around the extremity encompassing the site of healing area between bone segments 12. Connections are made to power source 17 and to analyzer 18. When power source 17 is activated, electric current pulses through active coil 16a, causing an induced electric current to flow in bone fixation plate 14. The induced electric current in bone fixation plate 14 produces a corresponding secondary induced current in passive coil 16b. Analyzer 18 measures the secondary induced current.

A reading from analyzer 18 is made while patient is at rest. A series of additional readings is made with increasing loads placed on healing area between bone segments 12. If loads increase to the point that analyzer 18 indicates strain on bone fixation plate 14, testing ceases. Analyzer 18 detects strain on bone fixation plate 14 by indicating a decrease in the secondary induced current in passive coil 16b compared to the resting state reading. This decrease in the secondary induced current results from the reduction in current flow through bone fixation plate 14, a property of its carbon nanotube component in response to strain from the applied load. The indication of strain shows that healing has not occurred sufficient to bear the load applied. The physician will then advise patient to engage only in activities producing a lesser load on bone fixation plate 14. Active patients would greatly appreciate knowing this limit. Additionally, the physician can encourage patient to engage in activities at a level that is safe as determined by the load applied prior to evidence of strain on bone fixation plate 14.

As healing area between bone segments 12 becomes stronger, the greater the load it can bear without causing strain on bone fixation plate 14. Bone healing may be considered complete when the maximum load supported by healing area between bone segments 12 is equal to the load that can be borne by the corresponding opposite side of the patient's body. Alternatively, healing may be considered complete when the maximum load not causing strain on bone fixation plate 14 approximates the load bearing capacity by similar, closely matched individuals. Such studies on normal individuals are commonly performed in medical research. At this point, physicians will know that the bone fixation device may be removed, if medically desirable.

Implanted bone fixation devices are subject to failure from breaking. This method will detect early evidence of loss of integrity of a bone fixation device. Any disruption of the carbon nanotube component of bone fixation plate 14 by even a partial break will cause an increase in electrical resistance at rest compared to past readings by analyzer 18. Similarly a loosened attachment screw 15, also having a component of carbon nanotubes, will cause an increase in electrical resistance to current flow in bone fixation plate 14. Prompt medical intervention and surgical revision of the repair will prevent extensive injury from an unexpected break of bone fixation plate 14.

Additional Embodiments

Bone fixation devices other than plates include rods, screws, nails, wires, clamps, prostheses, and others, any of which may incorporate carbon nanotubes or other high-aspect ratio, electrical conducting nano-particles, allow this method to measure the strength of healing.

Carbon nanotubes may be incorporated into resins such as polymethylmethacrylate described by Pienkowski, et al. in U.S. Pat. No. 6,872,403 (2005). Such resins may be used to stabilize repaired areas, allowing this invention to measure the strength of healing.

Some materials other than carbon form nanotubes that exhibit the electric current conduction properties in response to strain. These other materials may substitute for carbon and this invention will measure strength of healing.

The preferred embodiment emphasizes physicians and patients, but veterinary applications are obvious. Because test results are based on objective measurements of electric current changes through the bone fixation device, no response is required from the test subject.

Analyzer 18 may display the test result and sound an alarm when a load indicates strain on the bone fixation device. This will prevent injury from overloading the repaired area during testing.

Analyzer 18 may transmit test results to other external devices by direct or wireless communication permitting remote monitoring.

This method of measuring strength of healing may be used on patients not aware of pain due to treatment, medication, or illness. Pain sometimes provides a signal that a safe load limit has been reached or exceeded, but pain is unreliable for preventing further injury from overloading. Conversely, excessive fear of pain or fear of further injury may inhibit the patient from performing actions that are safe and beneficial to healing. This method for measuring strength of healing adds important information that will give confidence and encouragement to proper use of the repaired area during healing.

This method permits continuous monitoring for strain on bone fixation plate 14 by wearing testing cuff 16 while performing predetermined actions. An alarm on analyzer 18 can be made to sound when activity unexpectedly causes strain on the bone fixation device. Thus, advising patients on permissible activities and warning against excessively strenuous activities are based on objective, real-time test results.

This method is readily adaptable to external bone fixation devices. A carbon nanotube component incorporated in the rigid external bone fixation device permits testing for strain on the device with load bearing by direct contacts to an electric current source and to analyzer 18.

Similarly, direct measurement of electric current changes caused by strain as described for this method may be performed when bone fixation devices are implanted in sites where a detection cuff is not usable or the bone fixation device is very short. Electric leads attached to the ends of the bone fixation device may be brought to skin surface 13 where direct contact can be made for appropriate studies as described above. To reduce infection risk contact leads may remain below the skin surface where electrical contact can be made using sterile needles during testing. This is similar to the principle of implanting vascular access devices beneath the skin to minimize infection risk for patients receiving chemotherapy or renal dialysis.

When bone, ligament, or joint repairs require use of bone adhesives, the adhesives may be compounded to include carbon nanotubes as described by Pienkowski, et al. in U.S. Pat. No. 6,872,403 (2005). This method can then measure the strength of healing bone, ligament, joint, and related tissues.

This invention will measure bone strength in areas at high risk for fracture, such as brittle bones, by using limited surgery to attach a carbon nanotube-containing rigid rod to the bone in order to measure the limit of load capacity. This will allow the patient to know the safe level of activity similar to repaired bone areas.

It is feasible to inject carbon nanotube containing materials to stabilize weak areas of bones and ligaments. The present invention can be used to measure safe loads for these treated areas.

SUMMARY

The present invention permits non-invasive measurement of strength of healing at the site of bone repair by using rigid materials incorporating carbon nanotubes to stabilize the repair. This device can, with some modification, provide a means to measure bone healing in any area of the body. The present method will assess healing of joints or ligaments that have been repaired by rigid materials similar to bone fractures or resections. This device is safe since only graduated loads on the repaired area are used, thus minimizing risk of injury during testing. This device provides objective information not available by any method to measure healing of bone and related structures. The measurements by this device are important to patients who require guidance on limiting activities that may cause injury, as well as encouragement to engage in safe activities with confidence that injury will not occur. Thus, debilitating muscle atrophy from prolonged disuse during healing can be minimized. This invention provides real-time display of results on a continuous or episodic basis using appropriate alarm warnings when injurious loads are approached.

What is claimed is:

1. A method of measuring bone healing strength on a bone area being studied, comprising: a) implanting a bone fixation device constituted at least in part of a material selected from the group consisting of carbon nanotubes and other high aspect ratio materials which alter the conduction of electric current when said bone fixation device is subjected to stress or strain; b) applying externally a testing cuff requiring no direct electric contacts to said bone fixation device, wherein said testing cuff provides a means to cause an electric current in said bone fixation device, and to measure said electric current; c) using an analyzer to study changes in said electric current resulting from the effects of stress and strain on the material of the bone fixation device; d) obtaining a series of test results using predetermined loads on the bone area; and e) determining bone healing strength.

2. The method of claim 1 wherein an anchoring mechanism attaching said bone fixation device to said bone area contains a nanotube coating whereby loosening from said bone area will increase resistance to said electric current compared to a baseline reading.

3. The method of claim 1 wherein said bone fixation device is selected from the group of fixation devices including plates, pins, wires, rods, clamps and prostheses.

4. The method of claim 1 wherein said testing cuff includes an active coil with a means to produce a primary induced electric current in said bone fixation device.

5. The method of claim 4 wherein said testing cuff includes a passive coil with a means to produce a secondary induced electric current corresponding to said primary induced electric current.

6. The method of claim 1 further comprising: a) measuring said electric current while said bone area is at total rest; b) measuring said electric current with a plurality of predetermined loads on said bone area; and c) determining bone healing strength by noting a minimum load producing strain on the bone fixation device.

7. The method of claim 1 wherein said analyzer sounds an alarm when test results indicate strain on said bone fixation device; a) said analyzer having the capability of displaying test results; b) said analyzer having the capability of storing said test results; and c) said analyzer having the capability of transmitting said test results.

8. The method of claim 6 wherein said predetermined loads include weight bearing by the patient.

9. The method of claim 1 wherein said predetermined loads include a continuous, gradual increase in effort until an alarm sounds, whereby the patient will know a safe limit of exertion.

* * * * *